US011793655B2

(12) United States Patent
Shoshtaev (10) Patent No.: US 11,793,655 B2
(45) Date of Patent: **\*Oct. 24, 2023**

(54) STEERABLE SPINE IMPLANTS

(71) Applicant: LIFE SPINE, INC., Huntley, IL (US)

(72) Inventor: Eugene Shoshtaev, Del Mar, CA (US)

(73) Assignee: LIFE SPINE, INC., Huntley, IL (US)

( * ) Notice: Subject to any disclaimer, the term of this patent is extended or adjusted under 35 U.S.C. 154(b) by 646 days.

This patent is subject to a terminal disclaimer.

(21) Appl. No.: 16/837,627

(22) Filed: Apr. 1, 2020

(65) Prior Publication Data
US 2020/0222203 A1   Jul. 16, 2020

Related U.S. Application Data

(63) Continuation of application No. 15/957,893, filed on Apr. 19, 2018, now Pat. No. 10,617,534.
(Continued)

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30771* (2013.01); *A61F 2/446* (2013.01); *A61F 2/4465* (2013.01); *A61F 2/4611* (2013.01); *A61F 2/4603* (2013.01); *A61F 2002/3054* (2013.01); *A61F 2002/3082* (2013.01);
(Continued)

(58) Field of Classification Search
CPC ............ A61F 2/4455; A61F 2002/4475; A61F 2002/4627; A61F 2002/30387; A61F 2002/30507; A61F 2002/30607; A61F 2002/30367; A61F 2002/30372; A61B 17/7074; A61B 17/56; A61B 17/7067
See application file for complete search history.

(56) References Cited

U.S. PATENT DOCUMENTS 9,198,772 B2   12/2015   Weiman
9,204,972 B2   12/2015   Weiman et al.
(Continued)

FOREIGN PATENT DOCUMENTS

EP   2 535 021 A1   12/2012

OTHER PUBLICATIONS

International Search Report for International Application No. PCT/US2019/023446, dated Jun. 17, 2019, 6 pages.
(Continued)

*Primary Examiner* — Eduardo C Robert
*Assistant Examiner* — Tara Rose E Carter
(74) *Attorney, Agent, or Firm* — Foley & Lardner LLP (57) ABSTRACT

A spine implant (e.g., for a TLIF surgical procedure) is configured to be steered into place during implantation in conjunction with a complementary insertion instrument. The cage of the implant is constrained to a limited range of rotation about a post carried by the cage. The insertion instrument is configured to hold the post while controllably rotating the cage relative to the post in order to angularly position the implant during implantation. Range of rotational motion is controlled by the configuration of a groove in the post. A retaining pin of the implant extends from the cage into the groove of the post to rotationally connect the cage to the post.

17 Claims, 9 Drawing Sheets

Related U.S. Application Data (60) Provisional application No. 62/487,114, filed on Apr. 19, 2017.

(52) U.S. Cl.
CPC ............ *A61F 2002/3092* (2013.01); *A61F 2002/3093* (2013.01); *A61F 2002/30133* (2013.01); *A61F 2002/30153* (2013.01); *A61F 2002/30224* (2013.01); *A61F 2002/30405* (2013.01); *A61F 2002/30538* (2013.01); *A61F 2002/30593* (2013.01); *A61F 2002/30784* (2013.01); *A61F 2002/30904* (2013.01); *A61F 2002/4622* (2013.01); *A61F 2002/4625* (2013.01); *A61F 2002/4628* (2013.01); *A61F 2002/4629* (2013.01); *A61F 2310/00017* (2013.01); *A61F 2310/00023* (2013.01)

(56) References Cited

U.S. PATENT DOCUMENTS

| | | | |
|---|---|---|---|
| 9,554,918 B2 | 1/2017 | Weiman | |
| 9,770,343 B2 | 9/2017 | Weiman | |
| 9,931,226 B2 | 4/2018 | Kurtaliaj et al. | |
| 9,968,462 B2 | 5/2018 | Weiman | |
| 10,004,607 B2 | 6/2018 | Weiman et al. | |
| 10,617,534 B2 * | 4/2020 | Shoshtaev | A61F 2/4465 |
| 10,765,528 B2 | 9/2020 | Weiman et al. | |
| 10,874,522 B2 | 12/2020 | Weiman | |
| 10,874,523 B2 | 12/2020 | Weiman et al. | |
| 2009/0276049 A1 | 11/2009 | Weiland | |
| 2010/0256759 A1 | 10/2010 | Hansell et al. | |
| 2010/0256760 A1 * | 10/2010 | Hansell | A61F 2/4465 |
| | | | 623/17.11 |
| 2011/0276142 A1 * | 11/2011 | Niemiec | A61F 2/4611 |
| | | | 623/17.16 |
| 2013/0096685 A1 | 4/2013 | Ciupik et al. | |
| 2013/0103102 A1 | 4/2013 | Taylor et al. | |
| 2014/0058513 A1 | 2/2014 | Gahman et al. | |
| 2016/0045333 A1 | 2/2016 | Baynham | |
| 2016/0113776 A1 | 4/2016 | Capote | |

OTHER PUBLICATIONS

International Search Report for International Application No. PCT/US2018/028452, dated Jun. 22, 2018, 5 pages.

* cited by examiner

STEERABLE SPINE IMPLANTS

CROSS-REFERENCE TO RELATED PATENT APPLICATIONS

This U.S. non-provisional patent application is a continuation of U.S. application Ser. No. 15/957,893 filed on Apr. 19, 2018, which claims the benefit of and/or priority under 35 U.S.C. § 119(e) to U.S. provisional patent application No. 62/487,114 filed Apr. 19, 2017; the entire contents of both are hereby incorporated herein by reference.

BACKGROUND

The present invention relates to methods and devices for orthopedic surgery of the spine and particularly, to devices and methods for transforaminal lumbar interbody fusion (TLIF).

Many people contend with spine issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

A fusion of the lumbar region of the spine (a lumbar fusion) may be accomplished using several techniques. Once such technique is known as a transforaminal lumbar interbody fusion or TLIF. TLIF spine surgery is performed through the posterior aspect of the spine and provides stabilization of the anterior portion by an interbody cage and bone graft while the posterior portion is locked in place with pedicle screws, rods and bone graft. A TLIF procedure is advantageous over a posterior lumbar interbody fusion (PLIF) and other lumbar fusion procedures for several reasons. In a TLIF procedure, bone fusion is enhanced because bone graft is not only placed along the "gutters" of the spine posteriorly, but also in the disc space. A TLIF procedure also allows the surgeon to insert bone graft and an interbody cage into the disc space laterally from a unilateral approach without forcefully retracting the nerve roots as much as the PLIF approach, which can reduce injury and scarring around the nerve roots. However, there is room for improvement over current TLIF implants, instruments, and/or surgical procedures, such as the need to accurately place a TLIF implant into a vertebral space.

In view of the above, it is an object of the present invention to provide an improved TLIF implant, an instrument for implanting the improved TLIF, and/or a surgical procedure for the implantation. It is another object of the present invention to provide a steerable TLIF implant and instrument therefor.

SUMMARY

An implant, instrument, and procedure for a transforaminal lumbar interbody fusion (TLIF) is provided. A spine implant is configured to be steered into place during implantation in conjunction with a complementary insertion instrument. The cage of the implant is constrained to a limited range of rotation about a cylindrical post retained in the cage. The insertion instrument is configured to hold the post while controllably rotating the cage relative to the post in order to angularly position the implant during implantation. Range of rotational motion is controlled by the configuration of a groove in the post. A retaining pin extends from the cage into the groove of the post to rotationally connect the cage to the post.

The cage is preferably, but not necessarily, porous and has an end that is configured to axially receive the post and a bore in communication with the groove of the post, the bore receiving the retaining pin. The post includes a threaded hole in its side. An opening in the end of the cage allows access to the threaded hole of the post to allow a threaded rod of an installation instrument to attach to the post. The opening is configured to allow the cage to pivot to one side relative to the post when the post is connected to the threaded rod of the installation instrument. The length of the opening determines the amount of pivoting of the cage.

In one form, the cage has a generally linear body. In another form, the cage has a curved body.

The insertion instrument is characterized by an upper handle/knob supporting a hollow shaft. A rod having a threaded end extends through the hollow shaft, the threaded end of the rod configured to be threadedly received in the threaded bore of the post. Rotation of the upper handle/knob rotates the rod to thread (attach) or unthread (detach) the threaded end from the post. The insertion instrument also has a push rod detained in the inserter body via a dove-tailed articulation and actuated by a second or lower handle/knob. Actuation (rotation) of the lower knob translates the push rod to change the angular position of (angulate) the attached cage through rotation of the cage about the post.

In another form, the insertion instrument has two push rods detained in the inserter body via dove-tailed articulation that is actuated by the second or lower handle/knob. Actuation (rotation) of the lower know translates the two push rods to change the angular position of (angulate) the attached cage through rotation of the cage about the post Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate the present invention, wherein.

DETAILED DESCRIPTION

Figure 1:
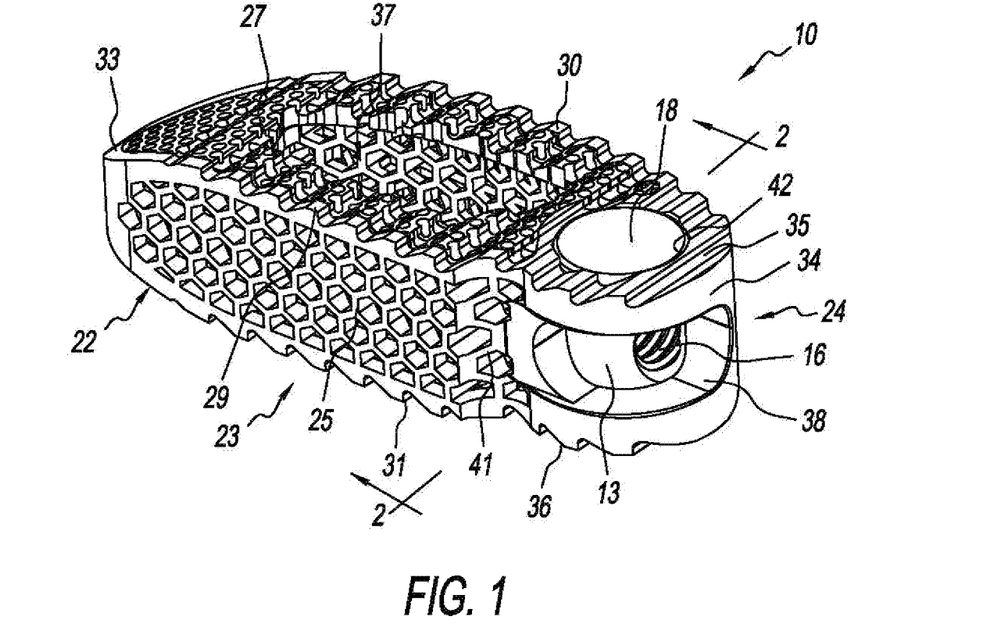
FIG. 1 is an isometric view of a steerable TLIF spine implant fashioned in accordance with the present principles.
Figure 2:
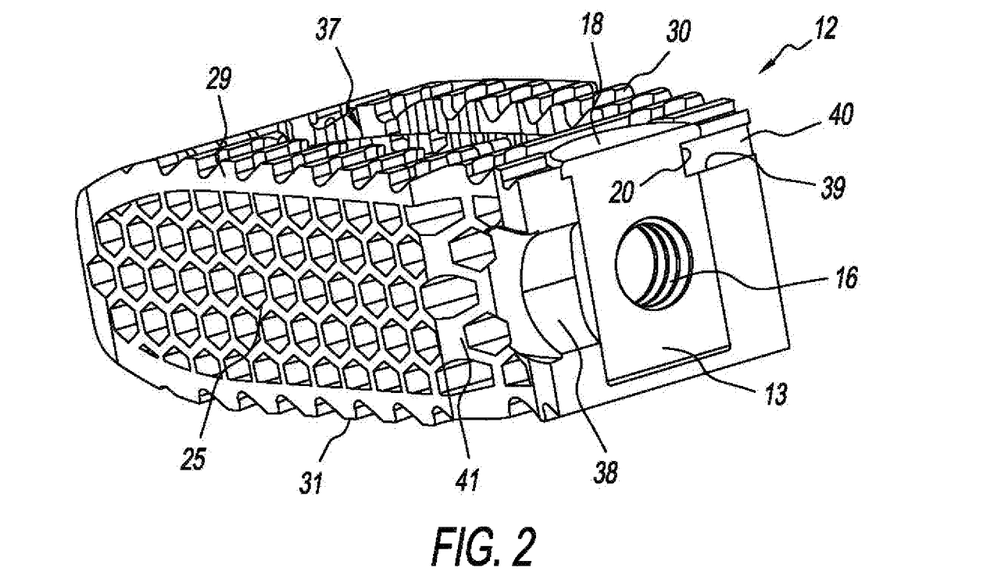
FIG. 2 is an isometric view of the steerable TLIF spine implant of FIG. 1 with a portion thereof in sectional.
Figure 3:
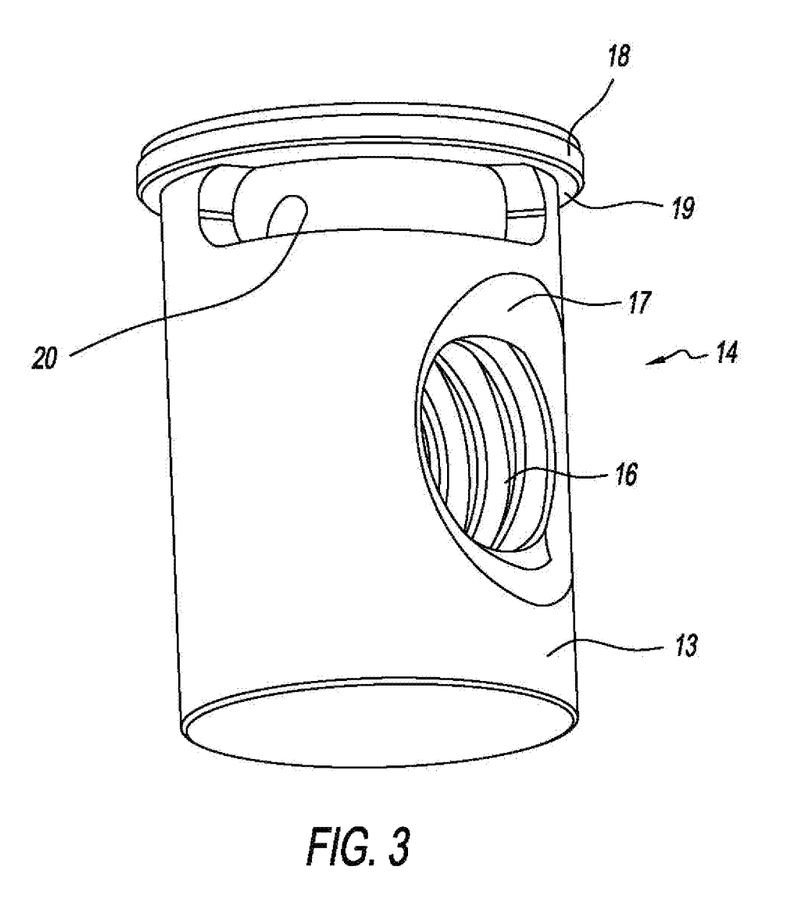
FIG. 3 is an enlarged isometric view of a post of the steerable TLIF spine implant of FIG. 1.

Referring to FIGS. 1-3, there is depicted an exemplary form of a transforaminal lumbar interbody fusion (TLIF) implant (spine implant), generally designated 10, fashioned in accordance with the present principles, that is able to be steered or guided into a vertebral space via an installation instrument. The TLIF implant 10 is made from a biocompatible material such as, but not limited to, titanium, stainless steel, an alloy of titanium or stainless steel, PEEK, solid PEEK, other plastics and polymers, and otherwise. The TLIF implant 10 is characterized by a cage or interbody device 12 and a post 14. The post 14 is preferably, but not necessarily, removable from and insertable into the cage 12 and allows the cage 12 to rotate relative to the post 14.

The post 14 is particularly shown in FIG. 3. The post 14 has a generally cylindrical body 13 with a head 18 on one end defining an under surface 19. As seen in FIG. 2, the under surface 19 is retained by a ledge of a bore of the cage 12. The post 14 also has a threaded hole 16 in its outer surface preferably, but not necessarily having a tapered region 17 surrounding the threaded hole 16. The tapered region 17 aids in receiving a threaded rod 53 of an insertion instrument 50. The post 13 further has a radial slot 20 in its outer surface that is preferably, but not necessarily, adjacent the under surface 19 of the head. The radial slot 20 has a length that determines the amount of rotation of the cage 12 about and relative to the post 13 as described herein. Changing the length of the slot 20 changes the amount of cage rotation/angulation. The longer the length, the greater the amount of rotation/angulation. The shorter the length, the lesser the amount of rotation/angulation. To this end, the cage 12 has a bore 39 that extends from the outer surface of the cage 12 to a large bore 42 of the head 34 of the cage 12. A retaining pin 40 is received in the bore 39 that extends into the large bore 42 of the head 34 and into the radial slot 20, thus rotationally constraining the rotation between the post 14 and the cage 12 to the arcuate length of the slot 20. The retaining pin 40 also axially retains the post 14 in the bore 42.

Referring back to FIGS. 1 and 2, the cage 12 is defined by a body 22 having a porous portion 23 that is shaped generally as a rectangle, and a head 24. The porous portion 23 is characterized by a generally sloped nose 33, an upper side 27, a lower side 28, a first lateral side 25, a second lateral side 26, a front or head 34, and a central cavity 37. The upper side 27 has a plurality of serrations, teeth or the like 35 along its length. The lower side 28 likewise has a plurality of serrations, teeth or the like 36 along its length. The serrations 35, 36 are angled to allow easy insertion of the cage 12 into a vertebral space (not shown), but inhibit its egress from the vertebral space (not shown).

The head 34 is generally round having an upper serrated surface 35 and a lower serrated surface 36. A large bore 42 is provided in the head 34 that extends from the upper serrated surface 35 to the lower serrated surface 36 and is sized to receive the post 14. The post 14 is rotatable in the bore 42 and thus relative to the cage 12. The cage 12 is rotatable relative to the post 14 when the post 14 is retained relative to the cage 12. The head 34 has a radial slot 38 in a front surface that is sized to allow access to the threaded bore 16 of the post 14. Changing the length of the slot 38 changes the amount of cage rotation and this angulation relative to the post 14. The longer the length, the greater the amount of rotation/angulation. The shorter the length, the lesser the amount of rotation/angulation. A notch 41 is provided at a lateral side of the head 34 that is configured to receive a pusher of the installation instrument.

Figure 4:
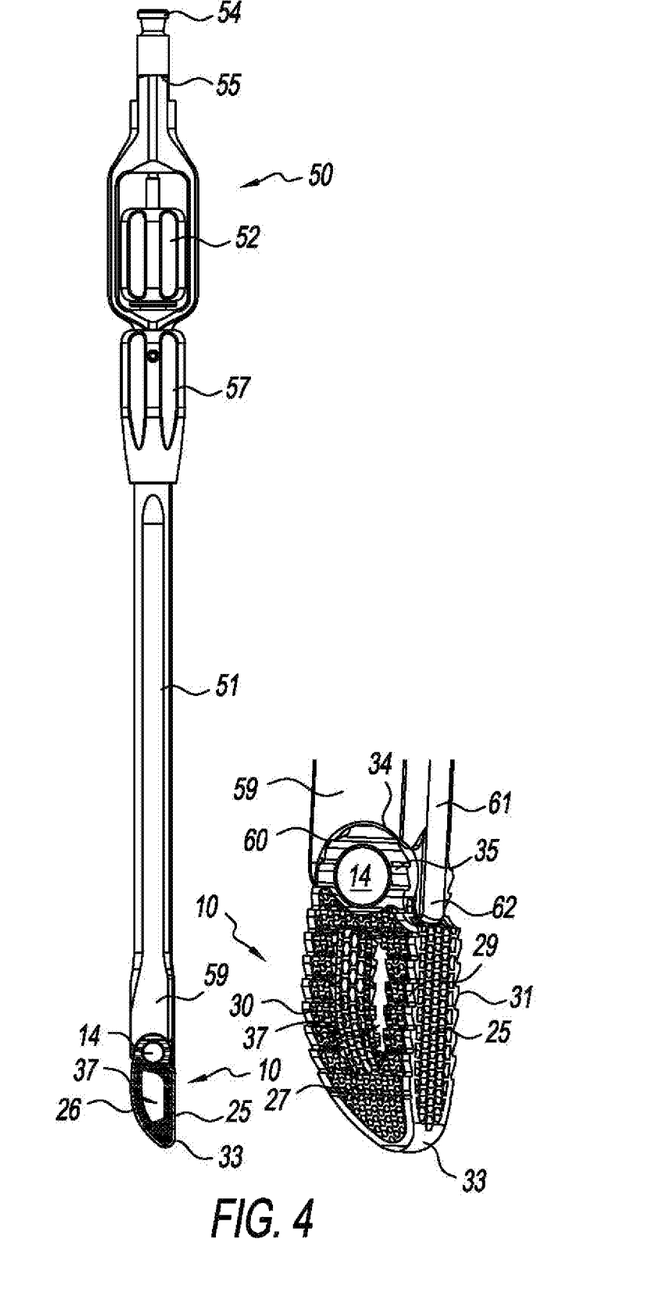
FIG. 4 is a combined illustration of a plan view of an inserter instrument for and attached to the steerable TLIF spine implant of FIG. 1, along with an enlarged isometric view of the steerable TLIF spine implant connected to the end of the inserter instrument, the steerable TLIF spine implant in an initial angular position and rotationally locked to the inserter instrument.
Figure 5:
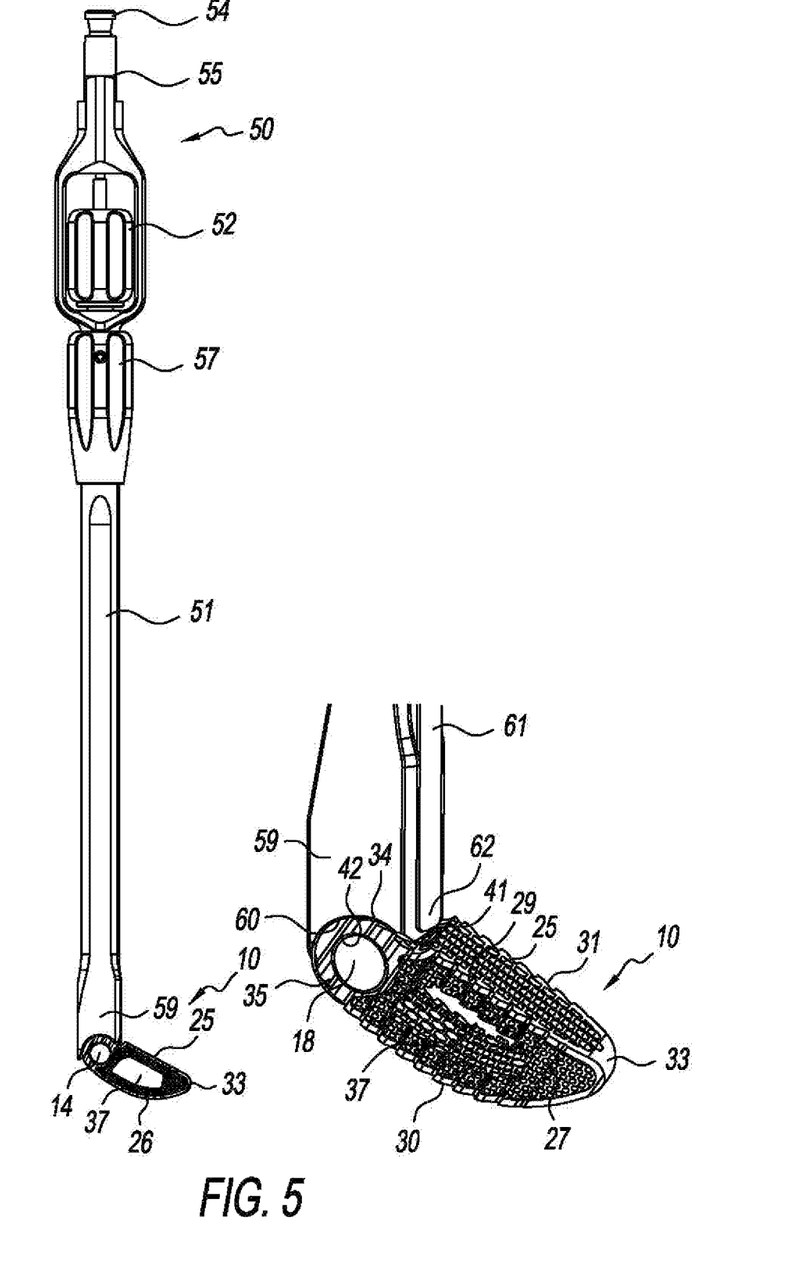
FIG. 5 is a combined illustration of a plan view of the inserter instrument for the steerable TLIF spine implant of FIG. 1, along with an enlarged isometric view of the steerable TLIF spine implant connected to the end of the inserter instrument, the steerable TLIF spine implant in a final angular position and rotationally unlocked from the inserter instrument.

Referring to FIG. 4 there is shown an installation instrument 50 for inserting the spine implant 10 within a vertebral space and angularly positioning/orientating the spine implant 10 into and/or within the vertebral space. In FIG. 4, the spine implant 10 is in an initial angular position and rotationally locked to an inserter/inserter portion 59 of the installation instrument 50. FIG. 5 shows the installation instrument 50 and the spine implant 10 in a final angular position and rotationally unlocked from the inserter 59 of the installation instrument 50.

Figure 6:
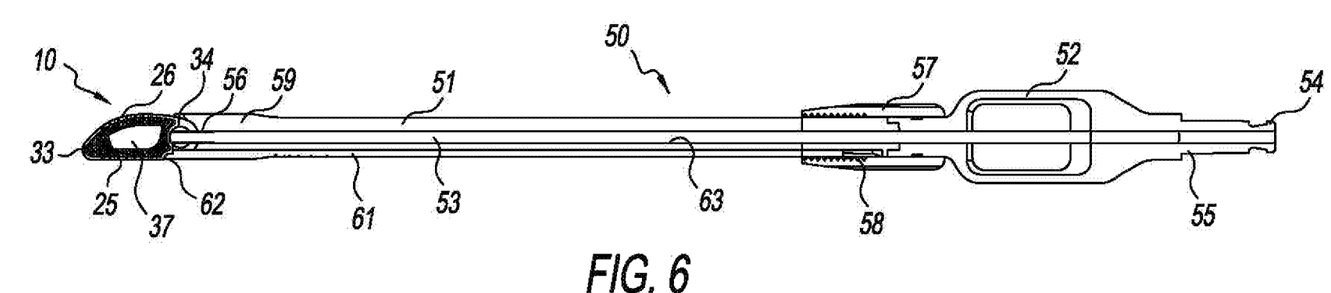
FIG. 6 is a sectional view of the inserter instrument of FIGS. 4 and 5 shown attached to the steerable TLIF spine implant of FIG. 1.
Figure 7:
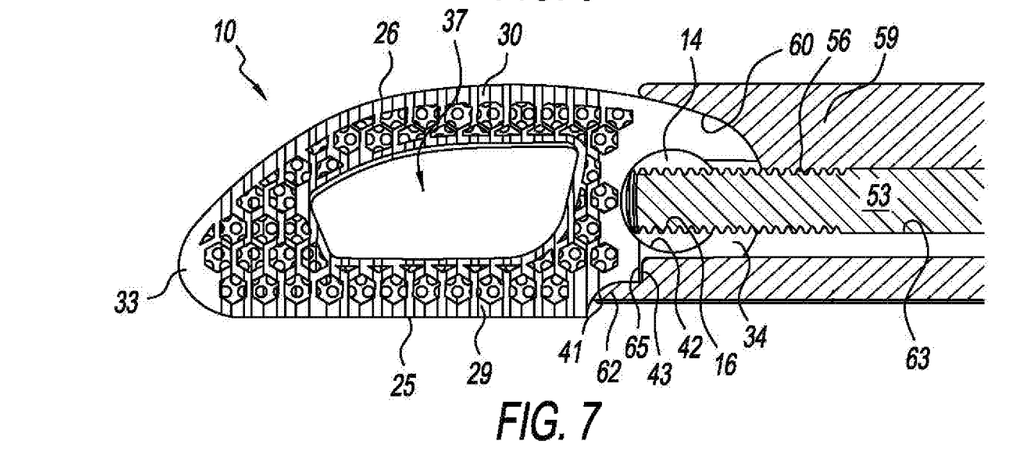
FIG. 7 is an enlarged sectional view of the end of the inserter instrument connected to the steerable TLIF spine implant of FIG. 1.

FIG. 6 shows the installation instrument 50 in sectional, while FIG. 7 shows a close-up the end of the installation instrument connected to the spine implant 10, both in sectional. A curved end portion 60 receives the curved head 34 of the implant 10. The installation instrument 50 has a shaft 51 that is connected to an upper handle 52 and having a longitudinal bore 63. A rod 53 extends through the bore 63 of the shaft 51 and has a knob 54 at a distal end 55, and threads at another end 56, the rod 53 axially movable relative to the shaft through rotation of the knob 54. In this manner the threaded end 56 of the rod 53 can be threaded into the threaded hole 16 of the post 14 (as shown in FIG. 7) by rotation in a first direction, or be unthreaded from the threaded hole 16 of the post 14.

Figure 8:
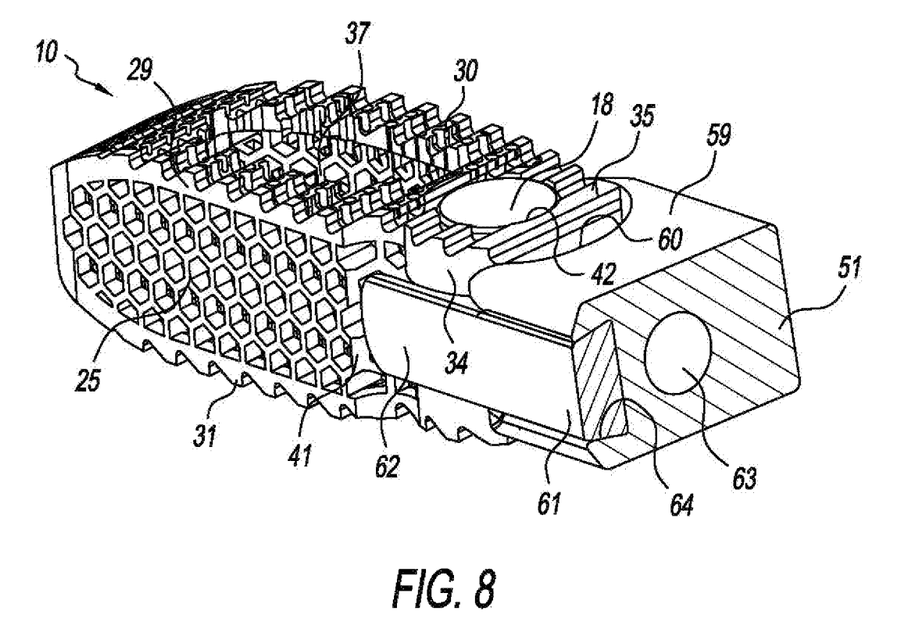
FIG. 8 is an isometric view of another steerable TLIF spine implant attached to an end of another inserter instrument with the end of the inserter instrument in sectional.

As depicted in FIGS. 7 and 8, the installation instrument 50 also has a pusher 61 that extends along the outside of the shaft 51 in a channel 64. The pusher 61 and the channel 63 are preferably, but not necessarily, of a dove-tail configuration. Other configurations may be used. The pusher 61 has a flanged end 62 that is received in the notch 41 of the implant 10. A shoulder 65 of the end contacts a ledge 42 of the notch 41. The pusher 61 is attached to the lower handle 57 such that rotation of the lower handle 57 axially moves the pusher 61. Inner threads 58 of the lower handle 57 interact with upper external threads of the shaft 51 to effect axial/longitudinal movement of the pusher 61 to lock and unlock rotation of the cage 10.

FIGS. 9-12 illustrate another form of a TLIF implant, generally designated 100, fashioned in accordance with the present principles. The TLIF spine implant 100 is characterized by a cage or interbody device 112 and a post 14a. The post 14a is preferably, but not necessarily, removable from and insertable into the cage 112 and allows the cage 112 to rotate relative to the post 14a.

Figure 12:
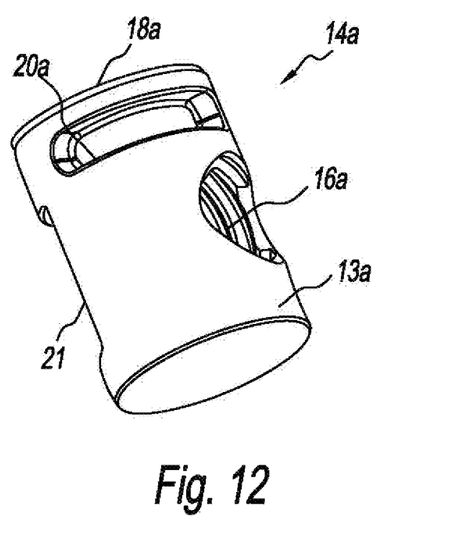
FIG. 12 is an enlarged isometric view of a post of the steerable TLIF spine implant of FIG. 8.

The post 14a is particularly shown in FIG. 12. The post 14a has a generally cylindrical body 13a with a planar head 18a on one end. The post 14a also has a threaded hole 16a in its outer surface preferably. The post 14a further has a radial slot 20a in its outer surface that is preferably, but not necessarily, adjacent the head 18a. The radial slot 20a has a length that determines the amount of rotation of the cage 112 about and relative to the post 14a as described herein. Changing the length of the slot 20a changes the amount of cage rotation/angulation. The longer the length, the greater the amount of rotation/angulation. The shorter the length, the lesser the amount of rotation/angulation. To this end, the cage 112 has a bore that extends from the outer surface of the cage 112 to a large bore 142 of the head 134 of the cage 112. A retaining pin 40 is received in the bore that extends into the large bore 142 of the head 134 and into the radial slot 20a, thus rotationally constraining the rotation between the post 14a and the cage 112 to the arcuate length of the slot 20a. The retaining pin 40 also axially retains the post 114 in the bore 142.

Figure 9:
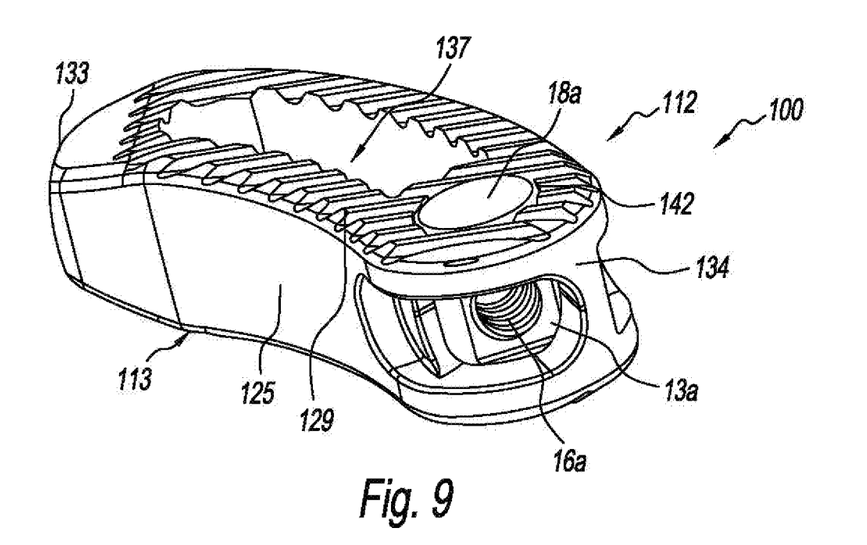
FIG. 9 is an isometric view of the steerable TLIF spine implant of FIG. 8.
Figure 10:
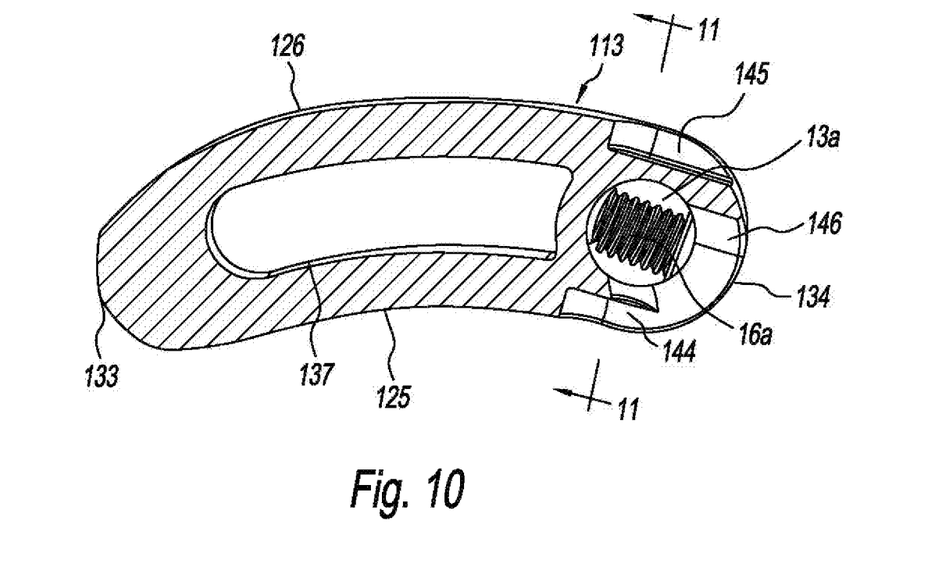
FIG. 10 is a sectional view of the steerable TLIF spine implant of FIG. 9.
Figure 11:
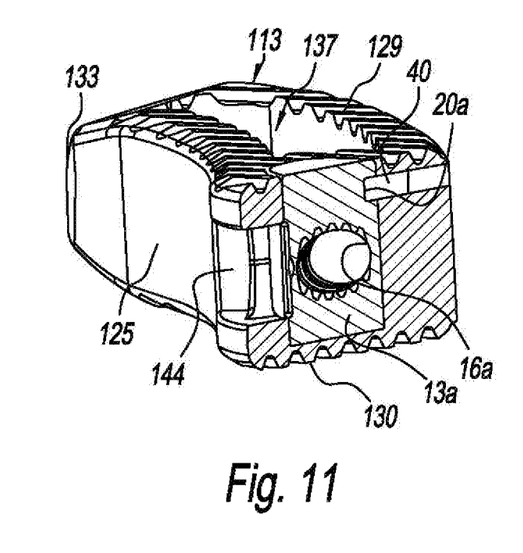
FIG. 11 is an isometric view of the steerable TLIF spine implant of FIG. 8 with an end thereof in sectional.

The cage 112 is defined by a body 113 that is shaped generally as an arch with a head 134. The body 113 is characterized by a generally sloped nose 133, a serrated upper side 129, a serrated lower side (not seen), a curved first lateral side 125, a curved second lateral side 126, a front or head 134, and a central cavity 137. The serrations of the upper and lower sides are angled to allow easy insertion of the cage 112 into a vertebral space (not shown), but inhibit its egress from the vertebral space (not shown).

The head 134 is generally round having an upper serrated surface and a lower serrated surface. A large bore 142 is provided in the head 134 that extends from the upper serrated surface to the lower serrated surface and is sized to receive the post 14a. The post 14a is rotatable in the bore 142 and thus relative to the cage 112. The cage 112 is rotatable relative to the post 14a when the post 14a is retained relative to the cage 112. The head 134 has a radial slot 144 in a front surface that is sized to allow access to the threaded bore 16a of the post 14a. Changing the length of the slot changes the amount of cage rotation and this angulation relative to the post 14a. The longer the length, the greater the amount of rotation/angulation. The shorter the length, the lesser the amount of rotation/angulation. A notch 145 is provided at a lateral side of the head 134 that is configured to receive a pusher of the installation instrument.

Figure 13:
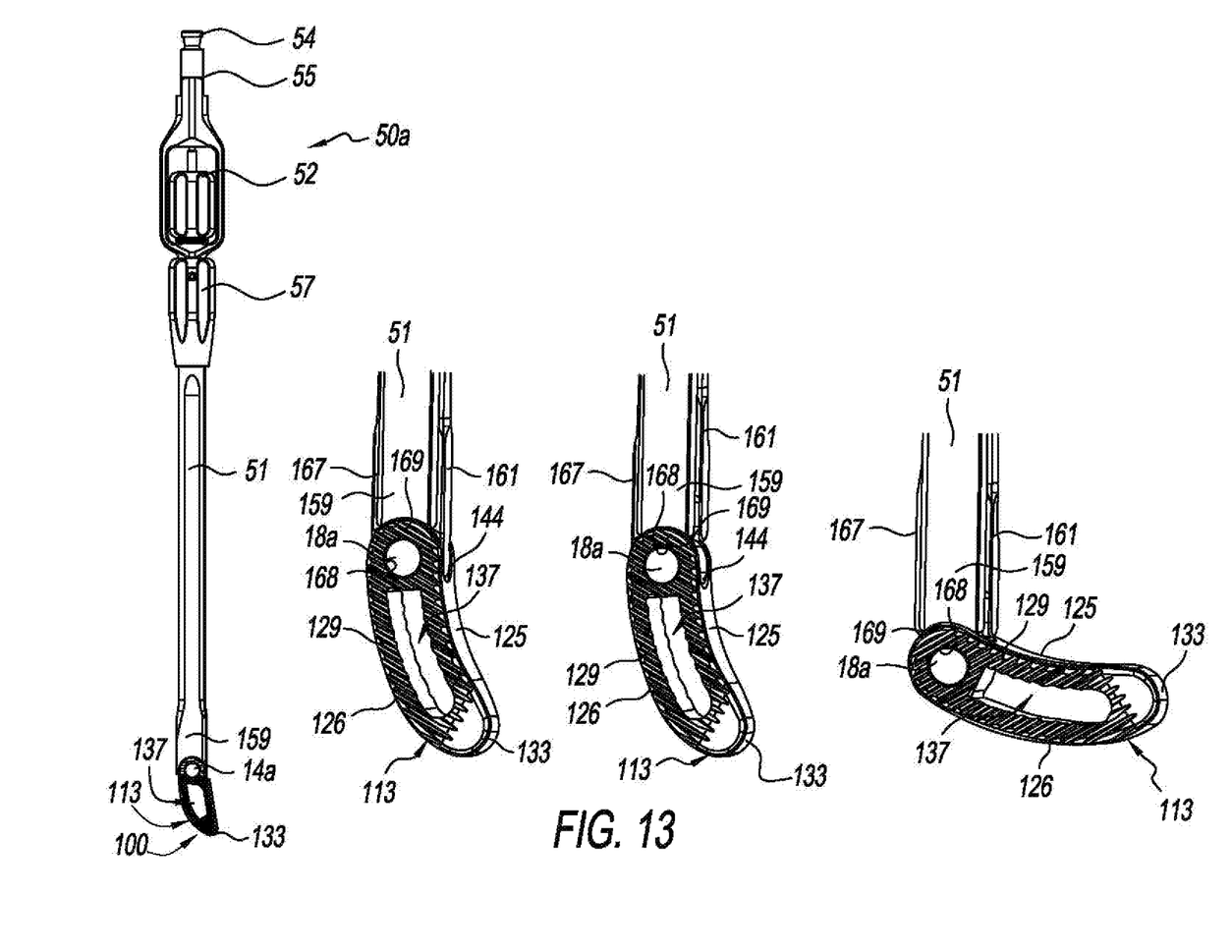
FIG. 13 is a combined illustration of the inserter instrument for and attached to the steerable TLIF spine implant of FIG. 8, along with a sequence of three enlarged views of the steerable TLIF spine implant of FIG. 8 on the end of the inserter instrument illustrating angular positioning of the steerable TLIF spine implant.

FIG. 13 provides a sequence of drawings illustrating the angulation ("steerability") of the TLIF spine implant 100 through implantation via an insertion instrument 50a, from an initial angular position through a final angular position. The insertion instrument 50a has the same features and components as the insertion instrument 50 but its inserter 159 includes first and second lateral pushers 161, 167. A curved end 169 of the inserter 159 mates with the end 168 of the implant 100, while the first and second lateral pushers 161, 167 are received in the lateral slots of the implant 100 to provide controlled angulation (angular positioning) of the implant 100. The implant 100 is received by the insertion instrument 50a through its threaded rod received in the threaded bore of the post 14a in like manner as the other TLIF spine implants discussed herein.

Figure 14:
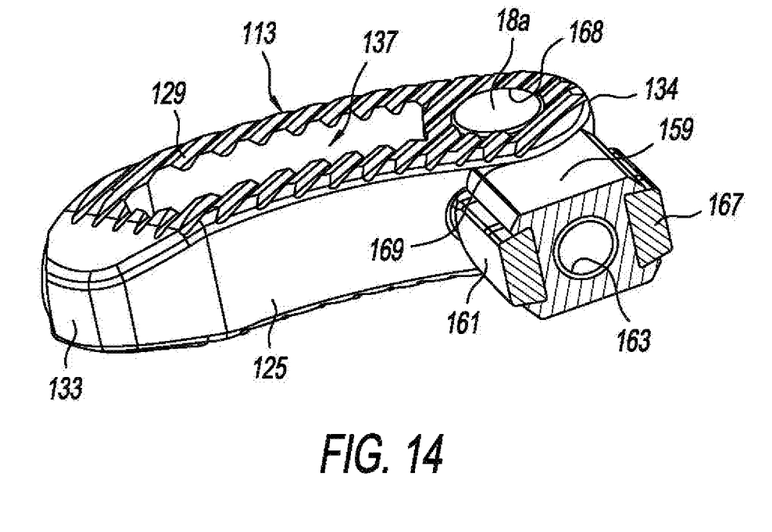
FIG. 14 is an isometric view of the steerable TLIF spine implant of FIG. 8 attached to an end of another inserter instrument, the end in sectional.

FIG. 14 shows the TLIF spine implant of FIGS. 9-13 with another version of an inserter 159 of an insertion instrument. The inserter 159 includes two (2) push rods 161, 167 that are retained in the inserter body via dove-tail axial translation and actuated by turning (rotating) the lower knob of the insertion instrument.

A method of installation includes placing a TLIF spine implant 10 onto the inserter instrument and initially locking rotation of the implant relative to the post. During insertion of the implant, the rotation is unlocked and the pusher rod(s) are used to angulate the implant.

It should be appreciated that dimensions of the components, structures, and/or features of the present TLIF spine implants and insertion instruments may be altered as desired within the scope of the present disclosure.

What is claimed is:

1. A spine implant comprising:
 a post comprising a hole configured to receive a rod of an installation instrument;
 a cage having an upper side, a lower side, a first lateral side, a second lateral side, a nose, a rear, and a central cavity, wherein the rear of the cage includes a first bore extending from the upper side towards the lower side, a second bore extending from the first lateral side into the first bore, and a radial slot providing access for the rod to attach to the hole in the post, wherein the post is inserted into the cage through the first bore such that the post is disposed in the rear of the cage and the cage is rotatable about the post; and
 a retaining component received in the second bore of the cage and configured to engage the post to constrain the cage to a range of rotation about the post.

2. The spine implant of claim 1, wherein:
 the post has a radial groove of a given length about its exterior surface; and
 the retaining component engages the radial groove, wherein range of rotational movement of the cage relative to the post is controlled by the given length of the radial groove of the post.

3. The spine implant of claim 2, wherein the given length of the radial groove determines amount of cage angulation.

4. The spine implant of claim 2, wherein the retaining component comprises a pin that is inserted in the second bore and at least partially disposed in the radial groove on the post.

5. The spine implant of claim 2, wherein the radial slot is configured to allow the cage to pivot to one side relative to the post when the post is connected to the rod of the installation instrument that extends through the radial slot.

6. The spine implant of claim 5, wherein the post is cylindrical, and the cage has a notch adjacent the rear that is configured to receive an angulation component of the installation instrument that controls angular position of the cage.

7. A kit for an interbody procedure, the kit comprising:
 an implant comprising:
  a post having an outer surface with a bore;
  a cage having an upper side, a lower side, a first lateral side, a second lateral side, a nose, a rear, and a radial slot in the rear, the post disposed in the rear of the cage such that the cage is rotatable about the post and the bore of the post is accessible through the radial slot of the cage; and a retaining pin received in the cage and in communication with the post to constrain the cage to a range of rotation about the post; and an installation instrument comprising:
a first handle supporting a hollow shaft;
a rod extending through the hollow shaft and having a first end, a second end, and a knob on the second end, the first end of the rod configured to be received in the bore of the post through the slot in the rear of the cage, wherein manipulation of the knob engages and disengages the first end of the rod with and from the bore of the post; and
a sleeve extending about the hollow shaft and connected to a slidable first member disposed in a first outside groove of the hollow shaft, wherein rotation of the sleeve translates the first member, and wherein the position of the first member relative to the cage is configured to allow or inhibit the attached cage to rotate about the post;
wherein the installation instrument further comprises a second member opposite the slidable first member, and wherein the position of the slidable first member relative to the second member allows rotation of the cage about the post.

8. The kit of claim 7, wherein the slidable first member is detained in the first outside groove of the hollow shaft via a dove-tailed configuration.

9. The kit of claim 7, wherein the first pusher is detained in the first outside groove of the hollow shaft via a dove-tailed configuration.

10. The kit of claim 7, wherein:
the post further comprises a radial groove of a given length about is exterior surface; and
the retaining pin is in communication with the radial groove, wherein range of rotational movement of the cage relative to the post is controlled by the given length of the radial groove of the post.

11. The kit of claim 10, wherein the given length of the radial groove determines amount of cage angulation.

12. The kit of claim 7, wherein:
the bore in the post is a threaded bore; and
the first end of the rod is threaded
the radial slot provides access to the threaded bore of the post to allow the threaded first end of the rod of the installation instrument to attach to the threaded bore of the post.

13. The kit of claim 7, wherein the radial slot is configured to allow the cage to pivot to one side relative to the post when the post is connected to the first end of the rod of the installation instrument that extends through the radial slot.

14. The kit of claim 7, wherein the cage has a notch adjacent the rear that is configured to receive an angulation component of the installation instrument that controls angular position of the cage.

15. A method of implanting an implant, the method comprising the steps of:
providing an implant comprising:
a post having an outer surface with a bore;
a cage having an upper side, a lower side, a first lateral side, a second lateral side, a nose, a rear, and a radial slot in the rear, the post disposed in the rear of the cage such that the cage is rotatable about the post and the bore of the post is accessible through the radial slot of the cage; and
a retaining component received in the cage and in communication with the post to constrain the cage to a range of rotation about the post;
providing an installation instrument for implanting the implant, the instrument comprising:
a first handle supporting a hollow shaft;
a rod extending through the hollow shaft and having a first end, a second end, and a knob on the second end, the first end of the rod configured to be received in the bore of the post through the radial slot in the rear of the cage, wherein manipulation of the knob engages or disengages the first end of the rod to and from the bore of the post; and
a sleeve extending about the hollow shaft and connected to a slidable first member disposed in a first outside groove of the hollow shaft, wherein rotation of the sleeve translates the slidable first member to allow or inhibit the attached cage to rotate about the post and change its angular position; and
steering the implant into a space using the installation instrument;
wherein the installation instrument further comprises a second member opposite the slidable first member, and wherein the position of the slidable first member relative to the second member allows or prevents rotation of the cage about the post.

16. The method of claim 15, wherein:
the post further comprises a radial groove of a given length about is exterior surface; and
the retaining component is at least partially engaged with the radial groove, such that a range of rotational movement of the cage relative to the post is controlled by the given length of the radial groove of the post.

17. The method of claim 16, wherein the given length of the radial groove determines amount of cage angulation.

* * * * *